United States Patent [19]

Kapitanov et al.

[11] 4,101,063
[45] Jul. 18, 1978

[54] SURGICAL INSTRUMENT FOR LIGATING TUBULAR ORGANS IN DEEP CAVITIES

[76] Inventors: Nikolai Nikolaevich Kapitanov, 8 ulitsa Oktyabrskogo polya, 5, kv. 9; Kim Nikolaevich Tsatsanidi, B. Cherkizovskaya ulitsa, 3, korpus 5, kv. 15, both of Moscow, U.S.S.R.

[21] Appl. No.: 768,365

[22] Filed: Feb. 14, 1977

Related U.S. Application Data

[63] Continuation of Ser. No. 659,520, Feb. 19, 1976, abandoned, which is a continuation-in-part of Ser. No. 609,893, Sep. 2, 1975, abandoned, which is a continuation of Ser. No. 463,795, Apr. 24, 1974, abandoned.

[30] Foreign Application Priority Data

Oct. 30, 1973 [SU] U.S.S.R. .................. 1974031

[51] Int. Cl.² ............................. B25C 1/00
[52] U.S. Cl. ................................ 227/19
[58] Field of Search ....................... 227/19

[56] References Cited

U.S. PATENT DOCUMENTS

| 3,482,428 | 12/1969 | Kapitanov et al. ............ 227/19 |
| 3,858,783 | 1/1975 | Kapitanov et al. ............ 227/19 |

*Primary Examiner*—Granville Y. Custer, Jr.
*Attorney, Agent, or Firm*—Holman & Stern

[57] ABSTRACT

A surgical instrument for ligating tubular organs in deep body-cavities in which there are three, elongated, mutually-movable, mutually-parallel elements one element carrying a magazine of U-shaped staples, another element including a movement-limiter serving as a pusher for forcing staples out of the magazine, and the third element serving as a supporting member fitted with a needle-shaped die formed as a hook for grasping and orienting the tubular organ being ligated; the element with the staple magazine having at its end a spring mechanism for pressing and fixing the grasped portion of the tubular organ being ligated as the first and third elements move relative to each other.

4 Claims, 17 Drawing Figures

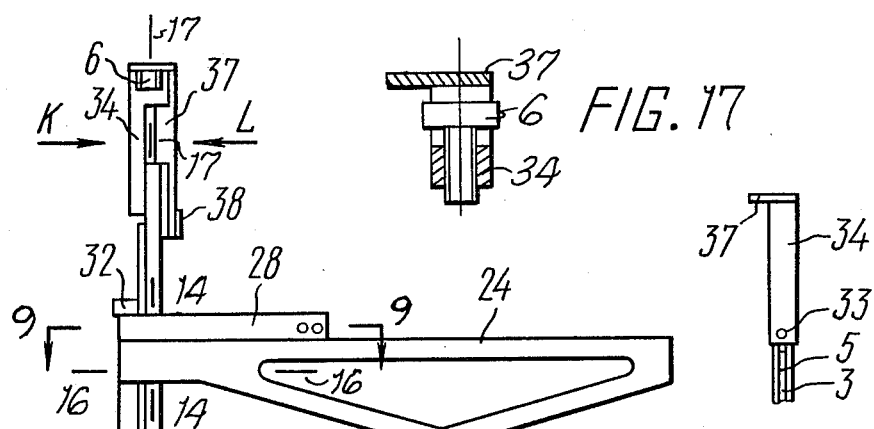
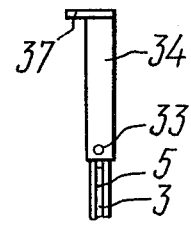
FIG. 17
FIG. 10
FIG. 11
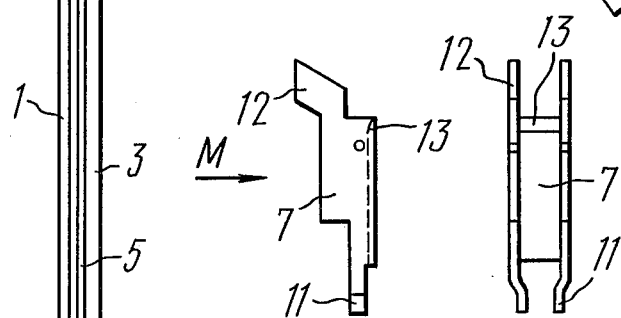
FIG. 12  FIG. 13
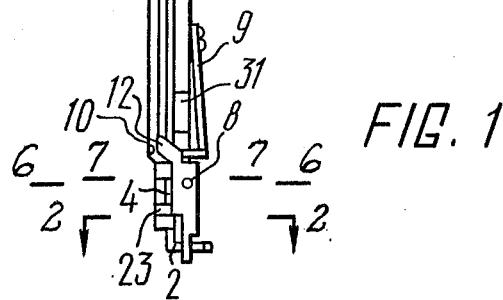
FIG. 1

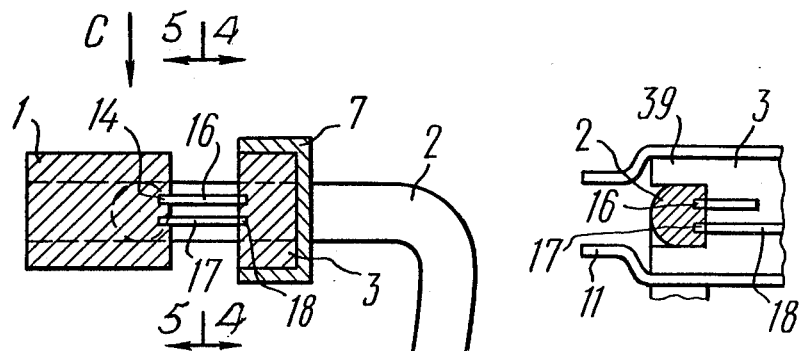
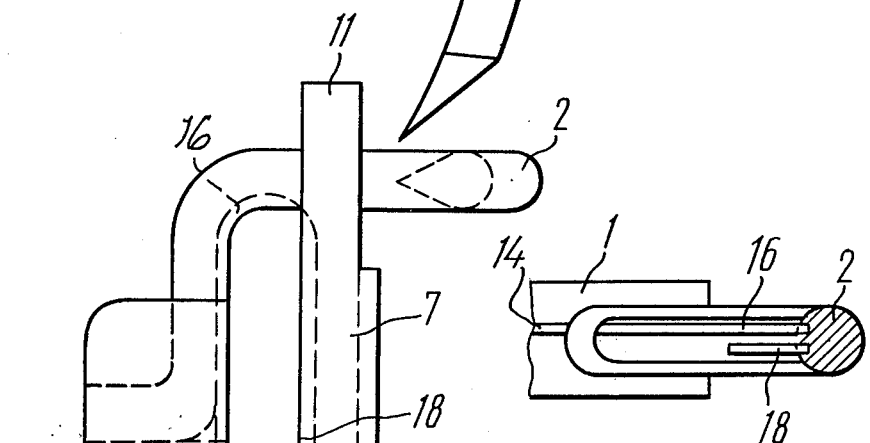
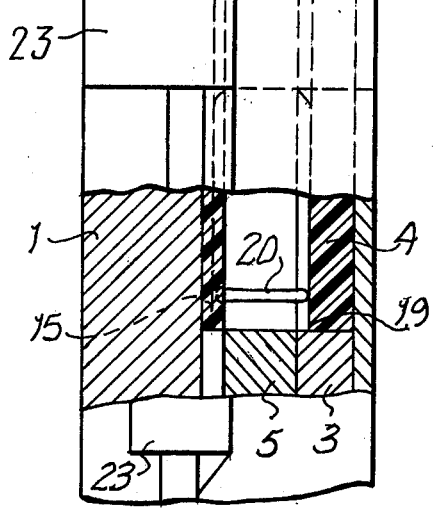

SURGICAL INSTRUMENT FOR LIGATING TUBULAR ORGANS IN DEEP CAVITIES

This is a continuation of application Ser. No. 659,520, filed Feb. 19, 1976, which in turn is a continuation-in-part of application Ser. No. 609,893, filed Sept. 2, 1975, which in turn is a continuation of application Ser. No. 463,795 filed Apr. 24, 1974; all are now abandoned.

INTRODUCTION

The present invention relates to surgical stitching instruments employed for stitching tubular organs in deep cavities, inter alia, for ligating varicose esophageal veins.

STATE OF THE ART

It is known in the art to employ a surgical instrument for suturing tissues with wire staples; see, for example, U.S. Pat. No. 3,482,428.

There also exist claws for ligating varicose vein portions in the course of surgical intervention employing transabdominal and transpleural approaches (see: M. D. Patsior et al., "Krovotechenie iz varikoznykh ven pishchevoda i zheludka" /Bleeding from Esophageal and Gastric Varicose Veins/, Meditsina Publishers, 1971).

It is likewise known in the art to employ a surgical instrument for suturing tissues with the aid of U-shaped staples i.e. U.S. Pat. Nos. 3,858,783 and 3,482,428 (USSR Inventor's Certificate No. 240,171) comprising a support case with a needle-shaped die with a groove formed in the inner surface thereof, a staple jaw with a magazine for U-shaped staples, a pusher and a pusher movement limiter. In the latter instrument, ligation of varicose esophageal veins requires opening of the thoracic and abdominal cavities.

OBJECTS OF THE INVENTION

It is an object of the present invention to obviate the foregoing and other disadvantages and provide means for securely ligating varicose esophageal veins without opening the thoracic and abdominal cavities.

The present invention provides a surgical instrument for ligating tubular organs in deep cavities, which is be capable of grasping a tubular organ disposed in a deep and narrow cavity in the tissue, bringing it to and pressing it against the die, and ligating it with the aid of a metal staple.

It is another object of the present invention to provide a surgical instrument for ligating tubular organs, wherein provision is made for ligation with the aid of a U-shaped staple by means of a single curved claw as well as for a directed movement of the staple toward the die.

It is yet another object of the present invention to provide a surgical instrument for ligating tubular organs in deep cavities, wherein provision is made for pressing and fixing the entire grasped portion of the tubular organ uniformly on both sides with the aid of a needle-shaped die, as well as for actuating the mechanism for pressing and fixing the grasped portion of the tubular organ against the die by moving the jaws carrying the staple magazine and the die relative to each other.

It is still another object of the present invention to provide a surgical instrument for ligating tubular organs in deep cavities, wherein provision is made for guarding against premature forcing of the staple out of the magazine.

It is a further object of the present invention to provide a surgical instrument for ligating tubular organs in deep cavities, wherein, should the instrument be employed together with an esophagoscope, provision is made for withdrawing the needle-shaped die from under the ligated vein.

It is herein contemplated that there shall be provided a surgical instrument for ligating tubular organs in deep cavities, wherein provision is made for convenient remote grasping and fixing of the tubular organ to be ligated.

In accordance with the present invention, the proposed surgical instrument for ligating tubular organs in deep cavities comprises a jaw carrying a magazine of U-shaped staples, a pusher for forcing the staples out of the magazine legs first, said pusher being provided with a movement limiter, and a supporting jaw carrying a needle-shaped die whereon the staples are bent in the course of ligation; the improvement consists in that the supporting jaw and the jaw which carries said staple magazine are formed as elements or rods arranged in parallelism, with the pusher rod being disposed therebetween, and the needle-shaped die is curved as a hook for grasping the tubular organ to be ligated which is disposed inside the tissue transfixed by the needle-shaped die as the instrument is turned about the longitudinal axis thereof, and the rod-shaped jaw carrying the staple magazine has a spring-loaded mechanism fastened at the end thereof, said spring-loaded mechanism serving to press the grasped portion of the tubular organ against the die and fix it as the jaws respectively carrying the staple magazine and the die execute motion relative to each other.

The foregoing improvement makes for convenient and secure ligation of tubular organs in deep and narrow cavities with the aid of a metal staple.

In accordance with an alternative embodiment of the invention, the surgical instrument is characterized in that two neighbouring parallel grooves are formed in the portion of the needle-shaped die which is oriented along the jaws making up the instrument, said two grooves serving as guides wherein the staple legs can move as far as the curved portion of the die to be bent thereon.

Said improvement permits ligating tubular organs in deep cavities with the aid of a U-shaped metal staple.

According to yet another embodiment of the invention, the surgical instrument is characterized in that the mechanism for pressing and fixing the grasped portion of the tubular organ is formed as a spring-loaded fork secured to the end of the magazine-carrying jaw which is immersed in the cavity; normally, said fork has its forked end spaced apart from the needle-shaped die and is thus able to freely grasp the hollow organ being ligated; further, the fork is provided with a stop coacting with the respective projection on the die-carrying jaw as the latter moved for turning the fork and setting it to a fixed position wherein the hollow organ is pressed by the fork against the needle-shaped die; said improvement permits ligating the entire grasped portion of the tubular organ.

In accordance with a further embodiment of the invention, the surgical instrument is characterized in that at the outer end of the element which constitutes the die-carrying jaw there is secured a handle oriented sidewise, and the outer ends of the magazine-carrying jaw and the pusher element or rod are interconnected by a latch capable of being set to two positions; in one position, both the elements slide together along the die-carrying element; in the other position, only the staple pusher element moves; said improvement permits preventing premature forcing of the staple out of the magazine, providing for improved reliability of the instrument.

And, finally, in accordance with the present invention, the proposed surgical instrument for ligating varicose esophageal veins, which is employed together with an esophagoscope through the bore whereof the rods or elements of the instrument are led to the varicose vein to be ligated, is characterized in that on the end of the inner tube of the esophagoscope, which is immersed in the esophageal cavity, there is formed a notch oriented along the tube axis, said notch being designed for accommodating the grasped tissue while the instrument is turned after the vein has been ligated, in such a manner that the tissue is securely held in the notch, enabling the needle-shaped die to be extracted from the tissue by turning the instrument backward; said latter improvement enables the needle-shaped die to be withdrawn from under the ligated tubular organ when ligating tubular organs through an esophagoscope.

BRIEF DESCRIPTION OF ACCOMPANYING DRAWINGS

The present invention will be further understood from the following detailed description thereof taken in conjunction with the accompanying drawings, wherein:

FIG. 1 is a general assembly view of a surgical instrument, showing the location of a staple magazine on the instrument in accordance with the invention;

FIG. 2 is an enlarged sectional view taken on the line 2—2 in FIG. 1;

FIG. 3 is a view taken from the direction of arrow C in FIG. with portions broken away and sectioned for purposes of clarity 2;

FIG. 4 is a sectional view taken on the line 4—4 in FIG. 2;

FIG. 5 is a sectional view taken on the line 5—5 in FIG. 2;

FIG. 10 is a fragmentary view looking from the direction of arrow K in FIG. 1;

FIG. 11 is a fragmentary view looking from the direction of arrow L in FIG. 1 (the pusher lock is shown removed);

FIG. 12 is an enlarged view of the movable bracket at the lower end of FIG. 1;

FIG. 13 is a view looking in the direction of arrow M in FIG. 12;

FIG. 17 is an enlarged fragmentary section taken substantially on line 17—17 of FIG. 1.

DESCRIPTION OF A PREFERRED EMBODIMENT

Figure 9:
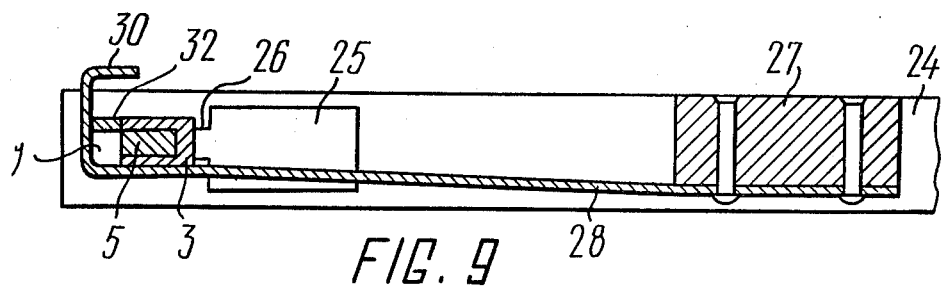
FIG. 9 is an enlarged sectional view taken on the line 9—9 in FIG. 1.
Figure 8:
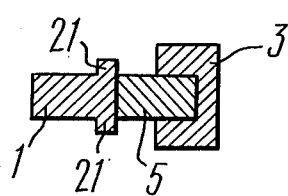
FIG. 8 is an enlarged sectional view taken on the line 8—8 in FIG. 1.
Figure 7:
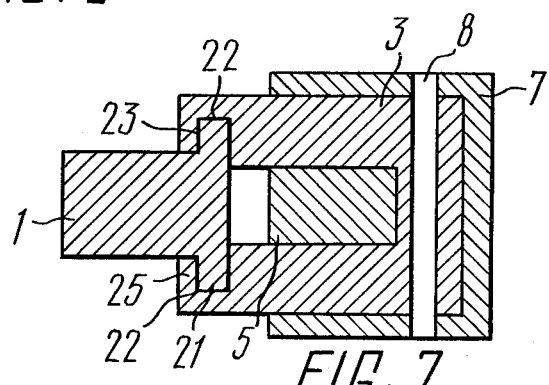
FIG. 7 is an enlarged sectional view taken on the line 7—7 in FIG. 1.

Referring now to the drawings, the instrument for ligating tubular organs in deep cavities comprises first, second and third elements or rods, said elements being formed as an elongated case 3, an elongated pusher 5 and an elongated rod 1, respectively, the rod 1 and case 3 being mutually parallel and the pusher 5 being disposed therebetween, as illustrated in FIG. 1. The rod 1 has at the end thereof a needle-shaped portion or die 2 for grasping the organs to be ligated, and the case 3 carries a magazine 4 for U-shaped staple, the magazine 4 being a replaceable member disposed above the die 2. As seen in FIG. 3, the pusher 5 serves to force the staples out of the magazine 4 (note there is shown in FIG. 3 the pusher 5, magazine 4 and a staple 20 in their reference position prior to the staple 20 being forced out of the magazine by the pusher 5,) and is provided with a movement-limiter 6 installed at the end thereof distal with respect to the die 2; the limiter 6 being formed as an adjustable screw. The adjustable limiter 6 for controlling the movement of pusher 5 is believed apparent from FIG. 17 which comprises a sectional view on line 17—17 at the upper end of FIG. 1. The screw 6 is installed on a bracket 34 fastened to the pusher 5 by means of an axle 33; see FIG. 10. Upon moving the bracket 34, and therefore the pusher 5, the end of the adjustable screw, engaging against the butt end of case 3 limits movement of the pusher 5.

A mechanism 7 for pressing a portion of the varicose vein to be ligated against the die 2 is installed on the case 3 near the lower end thereof.

As shown in FIGS. 1, 7, 12 and 13, the mechanism 7 includes a forked portion pivotally mounted in the case 3 on an axle or shaft 8. A spring 9, attached to the case 3, loads the forked portion of the mechanism 7. To be more precise, the forked portion has a pair of legs 11 facing inward (FIGS. 4 and 13) and a pair of projections 12 on the other ends thereof opposite with respect to the axle 8.

The projections 12 cooperate with two projections 10 (only one shown) (FIG. 1) formed on the rod 1. The forked portion of the mechanism 7 is further provided with a chamfer 13 (FIG. 13) serving to limit its pivotal angle rotation, as biased by the spring 9.

The fork portion of the mechanism 7 rotates on the axle being actuated by the spring 9. When the projections 12 do not abut against the projections 10, formed on the case 1 (which takes place when the case and the pusher are displaced toward a handle 24), the fork portion of the mechanism 7 is at an angle to the case 3 and rests with the chamfer portion 13 thereof on the case 3. The side of the chamfer portion 13 is such, that it enables the passage of the forked end of the legs 11, near the end of the needle-shaped die 2 from the internal side thereof and thus enables the moving of the entire portion of the tissue grasped by the needle-shaped die into the ligation zone.

Figure 6:
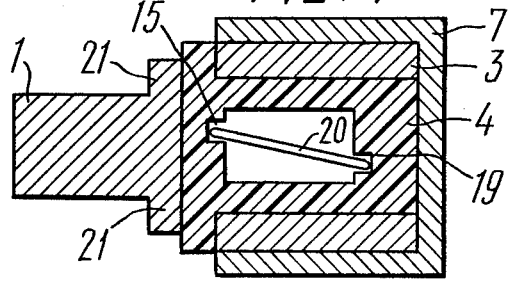
FIG. 6 is an enlarged sectional view taken on the line 6—6 in FIG. 1.

As shown in FIG. 6, the magazine 4 has an inner hole to allow passage of the pusher 5 and two lateral grooves 15 and 19 formed next to said inner hole as guides for the legs of a staple 20.

The rod 1 (FIG. 2) has a groove 14 reaching the groove 15 of the magazine 4 on one side, and a groove 16; as shown in FIG. 3, formed in the die 2 on the other side. The second groove 17 of the die 2 is formed next to the groove 16 in parallelism therewith, groove 18 in the case 3 communicating with groove 19.

The groove 18 of the case 3 extends as far as groove 19 of the magazine.

Further, as shown in FIGS. 1 and 6–8, on the side of the rod 1 facing the pusher, the case and the magazine there are formed two longitudinal diametrically opposite projections or flanges 21. In the zone of the magazine 4 the flanges 21 abut the side of the magazine 4 and; the flanges coact with notches 22 of projections 23 of the case 3; see FIG. 7, which is a sectional view of the projections 23. It can be seen in FIG. 8 that the flanges 21 adjoin the outer surface of the pusher 5.

Figure 16:
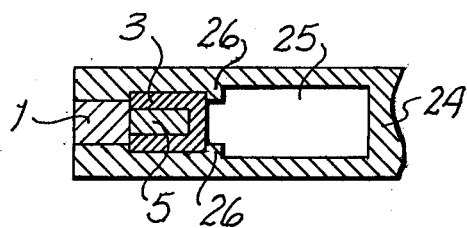
FIG. 16 is an enlarged fragmentary sectional view taken on line 16—16 of FIG. 1.

Handle 24 of the rod 1 is provided with an opening 25 wherethrough the case 3 may pass and its two projections 26 support the case 3; see FIG. 16, taken on section line 16—16 of FIG. 1.

The handle 24 is further provided with a projection 27 to which is secured a spring 28 (FIG. 9) which serves to fix the case 3 on the rod 1.

Figure 14:
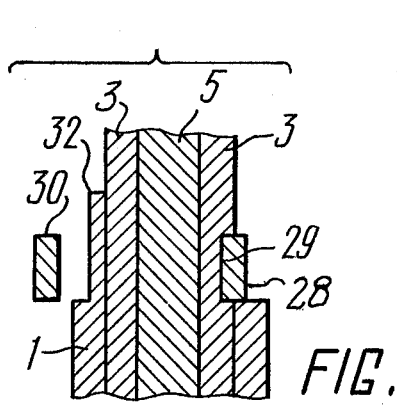
FIG. 14 is an enlarged sectional view taken on the line 14—14 in FIG. 1.

To be more precise, this is achieved by means of a notch 29 formed in the case 3 (FIG. 14) with the aid of the free end of the spring 28 which has a projection 30. Two symmetrical notches 31 (FIG. 1) formed on opposite sides (only one notch is shown) of the case 3 enable the case to pass between the projections 26 (FIG. 9) when the case and pusher are drawn up the rod from the FIG. 1 position.

The rod 1 has a projection 32 (FIGS. 9 and 14) for limiting the displacement of the spring 28.

As has been mentioned hereabove, the movement limiter 6 cooperates with the pusher; this is achieved by means of a bracket 34 fastened to the pusher by way of an axle 33 (FIG. 10), the bracket 34 being provided with an elongated slot 35 (FIG. 11) for accommodating the head of the screw 36 in the case 3. The limiter 6 formed as a screw is secured to the bracket 34, the limiter 6 being locked by a pusher latch 37 rotatably mounted on an axle 38. Reference is brought to FIG. 10, which is a view taken in the direction of arrow K in FIG. 1; the latch 37 and axle 38 are not shown in FIG. 10. Said FIG. 10 shows a bracket 34 secured by an axle 33 in the slot 35; above the bracket is shown a catch of the pusher latch 37. Swinging away of the latch 37 (FIG. 11) frees the pusher for limited longitudinal movement relative to the case, such movement being limited by the screw 6 and slot 35.

The lower end of the case 3 is provided with a forked portion 39 (FIG. 4) serving to coact with the die 2.

The instrument operates as follows:

First, the case 3 is detached from the supporting rod 1; to this end, it is necessary to press on the projection 30 of the spring 26 until it comes to rest against the projection 32, after which the case 3 is drawn out until the notches 31 are aligned with the projections 26, whereupon the case 3 is moved into the opening 25, and the case 3 is detached from the supporting rod 1. The magazine 4 is replaced by a new one, and, by pressing on the projection 30, the case 3 is attached to the supporting rod 1 in such a way that enough space is left between the needle-shaped die 2 and the case 3 for grasping tissue. In review the case 3 is drawn out in the direction opposite to the die 2; the case 3 and rod 1 are adapted to freely move relative to each other by release of spring 28 from slot 29. Then when the device is reassembled, the case is moved down the rod until the distance between their working ends is set at the surgeon's discretion and equals approximately 30 mm.

Holding the instrument by the handle 24, the vein is grasped at the site of ligation with the needle-shaped die 2. Then the case 3 is displaced along the supporting rod 1 toward the needle-shaped die 2. When the fork 11 is level with the needle-shaped die 2, the chamfer 13 of the mechanism 7 comes to rest against the projections 10 of the supporting rod 1, and the mechanism 7 starts rotating about the axle 8, compressing the varicose vein until the ends of the forks 11 and 39 are aligned in the same plane. As the case is displaced further, the die 2 enters the fork 39 of the case 3, while the spring 28 of the handle 24 simultaneously enters the notch 29. Now the instrument is ready for use. The latch 37 of the pusher is turned about the axle 38 away from the limiter 6 and, by pressing the bracket 34, the pusher 5 is pushed downward, causing the grasped vein portion to be stitched. In the process, the staple 20 is driven by the pusher into the grooves 18 of the case 3 and the grooves 14 of the supporting rod 1. As the staple moves further, one leg of the staple 20 enters the groove 16 of the needle-shaped die 2, while the other leg of the staple 20 enters the groove 17 of the needle-shaped die 2, and both the legs are bent. Upon completion of stitching, by pressing on the projection 30, the case 3 is retracted from the needle-shaped die 2 and the needle is withdrawn from under the stitched vein.

Figure 15:
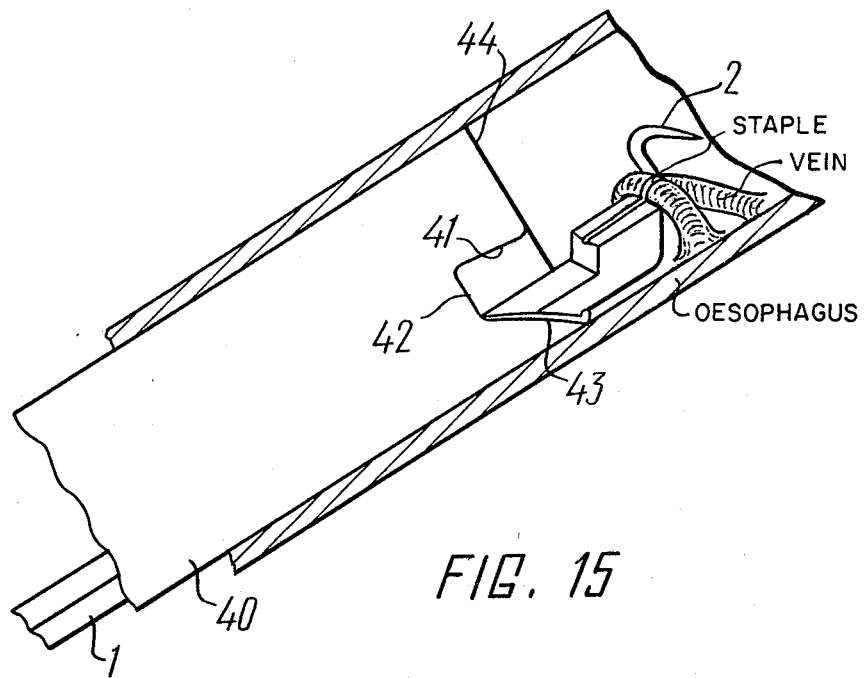
FIG. 15 is a fragmentary, prospective showing a supporting jaw in the middle tube of an esophagoscope before withdrawing the needle-shaped die out of the tissue.

In order to ligate varicose esophageal veins without opening the thoracic and abdominal cavities, the instrument for ligating veins is operated through an esophagoscope, e.g. Marzin's esophagoscope. See FIG. 15, which illustrates operation of the instrument through Merzin's esophagoscope mentioned above and described hereinafter.

Mezrin's esophagoscope comprises two tubes: an outer tube with a pin for connection with a handle (not shown), an inner tube 40 (FIG. 15) with a graduated spring for determining the depth of immersion of the tube, and a handle with a source of light and a mirror to direct the light beam (not shown in the drawing) into the inner tube 40. Face 44 of the distal end of the inner tube has a plane perpendicular to the tube axis.

In order to perform the ligation operation together with an esophagoscope, the end of the inner tube of the esophagoscope is brought to the ligation site. Then the instrument prepared for stitching is introduced into the esophagoscope, and the operation is performed under visual control. When the needle-shaped die emerges from the inner tube, the die is immersed with a rotary motion into the esophageal wall and the vein is grasped. After the vein is brought into the vicinity of the curved portion of the die, the case with the staple magezine is moved toward the die. As the case approaches the needle-shaped die, the springloaded fork leads entire vein into the ligation zone, after which the supporting rod and the staple magazine-carrying case are brought together. The latch of the pusher is then opened and, by pressing on the pusher, the ligation is performed. This completed, the staple magazine-carrying case is retracted from the needle-shaped die and, turning the instrument in a direction opposite to that in which the die was introduced into the tissue, the needle is drawn out of the tissue. But in order that the needle-shaped die may be extracted from the tissue, a tissue-pulling means is required. If the latter is not available, the tissue would not be detached from the needle-shaped die. So, to provide for tissue removal from the needle-shaped die immersed into the esophageal cavity, the end of the inner tube 40 of the esophagoscope is provided with a tissue-pulling means formed as a notch along the tube axis which is defined by three shearing lines, line 41 being disposed at an angle from the distal end to the proximal one, line 42 being disposed in a plane perpendicular to the tube axis, and line 43 being disposed in a helical path on the tube generator.

This arrangement of the shearing lines does not prevent the needle-shaped die from turning as it is introduced into the esophageal tissue and provides for the removal of the tissue from the needle-shaped die as the latter is withdrawn from the tissue. As the instrument is turned, the needle-shaped die together with the tissue is brought into the notch, the tissue comes to rest against the rib defined by the shearing line 41 and leaves the needle-shaped die.

What is claimed is:

1. A surgical instrument for ligating tubular organs in deep cavities of the human body, which comprises: in combination a first elongate element with opposite ends; a magazine containing a U-shaped staple mounted on said first element at one of the ends thereof; a second elongate element with opposite ends assembled next to and in parallelism with said first element, said second element comprising driving means for forcing said staple out of the magazine by longitudinal movement of said second element relative to said first element; a third elongate element assembled next to and in parallelism with said second element; a needle-shaped die secured to one of the ends of said third element and extending axially beyond said magazine for bending the staple forced out of the magazine by the driving means; said first and second elements being movable longitudinally in unison with respect to said third element; a spring-loaded mechanism movably mounted on said first element near said one of said ends thereof, said mechanism being operative to press and fix a portion of a tubular organ grasped by the die when the first and second elements are moved longitudinally with respect to the third element into an operative position with said mechanism adjacent said die; said needle-shaped die including a hook adapted to grasp the tubular organ while in tissue which the die pierces and while the first, second and third elements are manually rotated in said operative position about the longitudinal axis of the instrument, said second element in said operative position being longitudinally movable relative to said first and third elements to force the staple from the magazine, a movement-limiting means mounted on the opposite ends of the first and second elements for limiting the extent of movement of the second element relative to the first element: and cooperating groove means provided on said first element, the magazine, the third element and the die including portions permitting the legs of a staple to pass along the die as far as the hook on which the legs of the staple are bent when the staple is pushed out of the magazine by the driving means.

2. A surgical instrument as set forth in claim 1, wherein said spring-loaded mechanism incorporates a fork and wherein spring means is attached to the first element cooperating with said fork to move same away from the first element, a locking device on said mechanism, and a projection on the third element with which said locking device cooperates when the first and the third elements are moved one with respect to the other into said operative position in order to set the fork to a position in which the hollow organ can be pressed by the fork against the die.

3. A surgical instrument as set forth in claim 1 for ligating varicose esophageal veins, in combination with an esophagoscope having a tube through which the elements of the instrument are led to the varicose vein to be ligated, wherein the end of the tube, introduced into an esophageal cavity, has an open notch along the axis of the tube which accommodates a grasped tissue portion when the instrument is manually turned after ligation, so that the tissue is held in the notch, allowing the needle-shaped die to be withdrawn from the tissue by manually, reversibly turning the instrument.

4. A surgical instrument as set forth in claim 1 including a handle attached to the opposite end of said third element, means defining and opening through said handle, said first and second elements being accepted in said opening for longitudinal movement in unison relative to said third element, a spring member on said handle engaging said first element and being manually adjustable to control the movement of said first and second elements relative to said third element, and a latch pivoted on said first element adjacent the opposite end thereof, said latch being movable into and out of engagement with an end portion of said second element to control relative movements between said first and said second elements.

* * * * *